United States Patent [19]

Kennedy

[11] Patent Number: 4,814,405

[45] Date of Patent: Mar. 21, 1989

[54] TELECHELIC POLYMERS MADE FROM STERICALLY HINDERED BINIFERS

[75] Inventor: Joseph P. Kennedy, Akron, Ohio

[73] Assignee: University of Akron, Akron, Ohio

[21] Appl. No.: 223,085

[22] Filed: Jul. 22, 1988

Related U.S. Application Data

[62] Division of Ser. No. 638,034, Aug. 6, 1984, Pat. No. 4,767,885.

[51] Int. Cl.$^4$ .............................................. C08F 10/00
[52] U.S. Cl. .................................. 526/348.7; 528/392
[58] Field of Search ...................... 526/348.7; 528/392

[56] References Cited

PUBLICATIONS

Santos et al.; New Telechelic Polymers and Sequential Copolymers by Polyfunctional Initiator—Transfer—Agents (inifers), 40, Telechelic Polyisobutylenes by Sterically Hindered Binifers, Polym. Bull. (Berlin) 1984, 11(3), 261-7.

Kennedy, J. P. et al.; New Telechelic Polymers and Sequential Copolymers by Polyfunctional Initiator Transfer Agents (inifers), XXXVII, Telechelic Polyisobutylenes by Sterically Hindered Binifers, Initial Experiments; Polym. Mater. Sci. Eng. 1983, 49, 15-19.

Santos et al.; New Telechelic Polymers and Sequential Copolymers by Polyfunctional Initiator—Transfer—Agents (inifers), 42, Telechelic Polyisobutylenes by Brominated Inifers, Polym. Bull. (Berlin) 1984, 11(4), 341-8.

Primary Examiner—Joseph L. Schofer
Assistant Examiner—J. M. Reddick
Attorney, Agent, or Firm—Oldham & Oldham Co.

[57] ABSTRACT

Sterically hindered binifers are made as well as utilized to produce telechelic polyisobutylenes. The telechelic polymers can be produced at high temperatures, for example minus 30° C.

10 Claims, No Drawings

TELECHELIC POLYMERS MADE FROM STERICALLY HINDERED BINIFERS

This is a division of application Ser. No. 638,034, filed Aug. 6, 1984, now U.S. Pat. No. 4,767,885.

TECHNICAL FIELD

The present invention relates to sterically hindered binifers and to polyisobutylene telechelic polymers made therefrom.

BACKGROUND ART

Heretofore, telechelic polymers have been made through cationically polymerizable olefin monomers having from 2 to about 6 terminal halogens. The telechelic halogenated polymers are formed by reacting the monomers with an initiator transfer agent, having at least 2 tertiary halogens, and under cationic polymerization conditions as set forth in U.S. Pat. No. 4,276,394.

U.S. Pat. Nos. 4,316,973 and 4,342,849 relate to the preparation of a telechelic diolefin polyisobutylene by refluxing a solution of telechelic dihalogen polyisobutylene, adding a solution of a strong base such as potassium t-butoxide and stirring to form the telechelic diolefin polyisobutylene.

U.S. Pat. No. 4,429,099 relates to preparing a telechelic prepolymer which is phenol terminated.

DISCLOSURE OF INVENTION

It is therefore an aspect of the present invention to produce sterically hindered binifers such as 1,3-di(2-chloro-2-propyl)-5-tertbutylbenzene, that is m-t-BuDCC, 3-di(2-bromo-2-propyl)-5-tert-butylbenzene, that is m-t-BuDCB, 1,3-di(2-chloro-2-propyl)-4,6-dimethylbenzene, that is m-DMeDCC and 1,3-di(2-bromo-2-propyl)-4,6-dimethylbenzene, that is m-DMeDCB.

It is yet a further aspect of the present invention to utilize sterically hindered binifers, as above, to prepare telechelic polymers therefrom.

It is a still further aspect of the present invention to utilize sterically hindered binifers, as above, in forming telechelic polymers in which the monomer utilized is isobutylene.

These and other aspects of the present invention will become apparent from the following detailed specification.

In general, a sterically hindered binifer comprises: the binifer having the formula

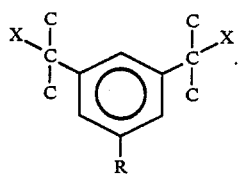

where R is an alkyl having from 1 to 15 carbon atoms, or a cycloalkyl having from 4 to 8 carbon atoms, and where X is Cl or Br.

Additionally, a sterically hindered binifer comprises: the binifer having the formula

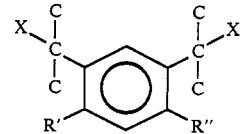

where R' and R" can be the same or different, wherein R' and R" is an alkyl having from 1 to 5 carbon atoms, a cycloalkyl having from 4 to 8 carbon atoms, and wherein X is chlorine or bromine.

In general, a telechelic polymer prepared from a sterically hindered binifer, comprises: the polymer, said polymer made by reacting isobutylene with the sterically hindered binifer, said sterically hindered binifer has the formula

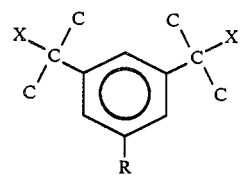

where R is an alkyl having from about 1 to about 5 carbon atoms or a cycloalkyl having from 4 to 8 carbon atoms, where X is chlorine or bromine.

Additionally, a telechelic polymer has the formula

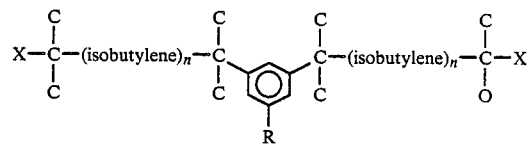

where R is an alkyl having from 1 to 5 carbon atoms or a cycloalkyl having from 4 to 8 carbon atoms, where X is chlorine or bromine, and wherein n is from 1 to 25,000.

In addition, a telechelic polymer has the formula

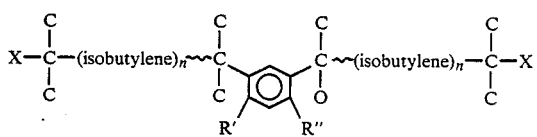

wherein R' and R" can be the same or different, wherein R' and R" is an alkyl group having from 1 to 5 carbon atoms or a cycloalkyl group having from 4 to 8 carbon atoms, wherein X is chlorine or bromine, and wherein n is from 1 to about 50,000.

BEST MODE FOR CARRYING OUT THE INVENTION

A sterically hindered binifer is defined as a binifer in which, due to the presence of a substituent, indanyl skeleton formation is prevented during the first propagation step of isobutylene polymerization.

According to the present invention, four unique sterically hindered binifers are produced. They are 1,3-di(2-chloro-2-propyl)-5-tert-butylbenzene, that is m-t-BuDCC, 1,3-di(2-bromo-2-propyl)-5-tert-butylbenzene, that is m-t-BuDCB, 1,3-di(2-chloro-2-propyl)-4,6-dimethylbenzene, that is m-DMeDCC and 1,3-di(2- bromo-2-propyl)-4,6-dimethylbenzene, that is m-DMeDCB.

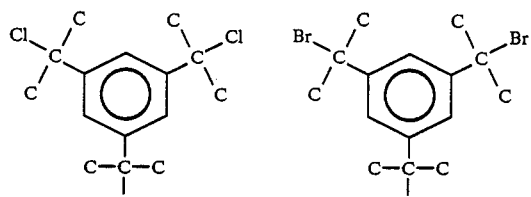

m-t-BuDCC     m-t-BuDCB

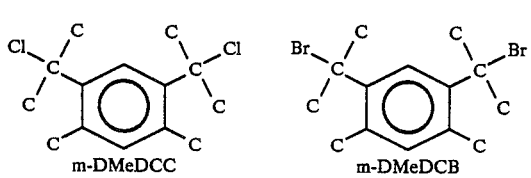

m-DMeDCC     m-DMeDCB

Although the hydrogen groups have been left out in all formulations of the present invention, it is understood that this is only for sake of convenience that they are contained within the compounds. The synthesis of the first two compounds is as follows, the starting compound, meta diisopropyl benzene, Formula I, is placed in the vessel at a low temperature, desirably from about minus 20° C. to about 30° C., with from about minus 5° C. to about 5° C. being preferred.

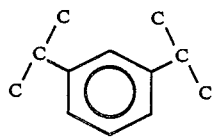

Formula I

To this compound is added a molar excess, for example, from about 2 to about 3 molar excess of tert-butyl chloride, or other chlorinated alkanes having 4 to 8 carbon atoms. Tert-butyl chloride is preferred. Additionally, a catalyst such as $FeCl_3$ is utilized in a molar excess as in an amount of from about 2 to about 3, with from about 1.6 to about 1.8 being preferred. After the evolution of HCl, the mixture is washed with water and dried with a desiccant, e.g., $CaCl_2$ and distilled under vacuum. The product is relatively pure meta diisopropyl benzene with a sterically hindered tertiary butyl group chemically bonded thereto, Formula II.

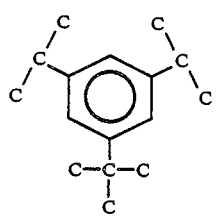

Formula II

In order to add bromide to the isopropyl groups of the compound, from about 2 to about 3 moles, and preferably from about 2.1 to about 2.3 moles per mole of sterically hindered compound of a brominated succinimide is added. An example of such as succinimide includes N-bromo-succinimide. Additionally, small amounts of peroxide such as benzoyl peroxide as from about 0.01 to about 0.03 moles in a suitable solvent such as a polar halogenated solvent, for example, carbon tetrachloride are added. The solution is allowed to reach its boiling point at which time it is cooled with ice, filtered, the solvent evaporated, the product recrystallized from n-hexane. The product is essentially that set forth in Formula III.

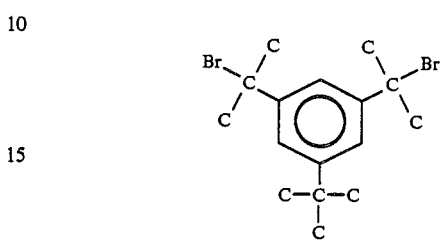

Formula III

The compound of Formula III is one of the binifers of the present invention, 1,3-di(2-bromo-2-propyl)-5-tert-butylbenzene, that is m-t-BuDCB. In order to produce the corresponding binifer containing chloro groups thereon in lieu of bromo groups, the compound of Formula III is then dehydrobrominated with a strong base, such as t-butyl hydroxide. Thus an excess of potassium t-butoxide in the amount of from 2 to about 6 moles, and preferably from about 3 to about 5 moles per mole of a compound of Formula III is added dropwise to the solution of Formula III and tetrahydrofuran over a period of 30 minutes. The initial addition temperature is generally from about minus 5° C. to about 5° C. The mixture is then slowly warmed to room temperature over a matter of from about 4 to about 6 hours. Once ambient temperature is reached, approximately 400 to about 700 grams of a hydrocarbon solvent such as n-hexane is added. The product is then washed with water, dried, and vacuum distilled. An essentially pure compound, having Formula IV was obtained.

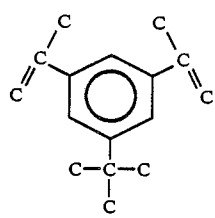

Formula IV

The desired 1,3-di(2-chloro-2-propyl)-5-tert-butylbenzene, m-t-BuDCC, is obtained by hydrochlorination of the compound of Formula IV. Thus excess HCl is bubbled through a solution of the compound Formula IV in an amount of from about 0.03 to about 0.07 moles, with from about 0.04 to about 0.06 moles being preferred in a suitable halogenated hydrocarbon solvent such as dichloromethane at a temperature of from about minus 10° C. to about 10° C. and preferably from about minus 5° C. to about 5° C. for a period of time as from about 4 to about 10 hours. The solvent is then removed and the product recrystallized from n-hexane. The result was a pure m-t-BuDCC, Formula V.

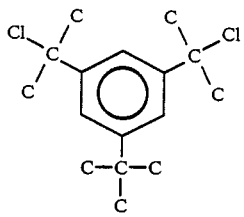

Formula V

The preparation of m-DMeDCC and m-DmeDCB is as follows: meta-xylene was diacetylated to produce 1,3-dimethyl-4,6-diacetophenone. The product was then purified by recrystallization from an ether, for example, diethyl ether, followed by sublimation. The 1,3-dimethyl-4,6-diacetophenone was converted into 1,3-di(2-hydroxy-2-propyl)4,6-dimethylbenzene by a Grignard ($CH_3MgI$/ether) reaction. The product was recrystallized from an ethyl acetate solution. This compound was then hydrochlorinated to produce m-DMeDCC. The hydrochlorination step can be carried out as by utilizing HCl gas in a chlorinated hydrocarbon such as $CH_2Cl_2$ for a period of from about 4 to about 8 hours at a temperature of from about minus 5° to about 5° C. Similarly, m-DMeDCB is produced by hydrobromination in the same manner as hydrochlorination is carried out as by utilizing HBr gas, or the like. The formulas for m-DMeDCC and m-DMeDCB are as follows:

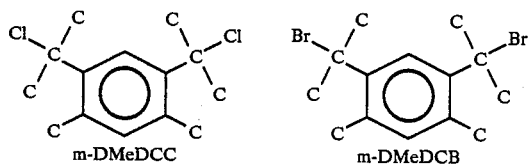

In a similar manner, compounds made having the formulation of Formula VI can also be made.

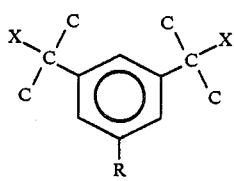

Formula VI

R of Formula VI is an alkyl having from 1 to 5 carbon atoms or a cycloalkyl having from 4 to 8 carbon atoms. X is either a chlorine group or a bromine group. Similarly, binifers having the structural formulation set forth in Formula VII can also be made in a manner as set forth above.

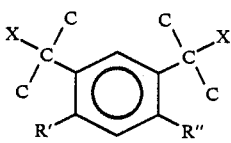

Formula VII

In Formula VII, X is a chlorine group or a bromine group and R' and R" can be the same or different. More specifically, R' and R" is an alkyl group having from 1 to 5 carbon atoms or a cycloalkyl group having from 4 to 8 carbon atoms.

According to the concepts of the present invention, isobutylene can be polymerized off of the binifers commencing at each functional side group thereon. Utilization of sterically hindered binifers has been found to prevent the formation of indanyl rings which otherwise would lead to useless isobutylene polymers that do not contain functional end groups. Moreover, the polymerization temperature can be much higher than otherwise.

A Lewis acid is utilized as a catalyst in the polymerization of isobutylene. Examples of such catalysts include $SnCl_4$, $TiCl_4$, $AlCl_3$, $FeCl_3$, and $BF_3$ with $BCl_3$ being preferred. The amount of catalysts utilized is a mole equivalent excess based upon the equivalent amount of binifer. Desirably, from about 5 to about 10 equivalence of the catalyst is utilized per equivalent of binifer. The isobutylene polymerization is generally carried out in the presence of a halogenated, preferably chlorinated hydrocarbon solvent such as methyl chloride, ethyl chloride, butyl chloride, dichloromethane, 1,1-dichloroethane, and the like. The concentration of the isobutylene in the solution along with the catalysts is usually from about 0.1 to about 1 mole per liter of solution. Polymerization is generally carried out at a temperature of from about minus 20° C. to about minus 80° C. with from about minus 30° C. to about minus 50° C. being preferred. The polymerization is initiated at the site of the halogen on the binifer, for example at the tertiary chloro group. The total number of isobutylene repeating groups emanating from the inifer can range from about 2 to about 50,000 and preferably from about 2 to about 200. That is, each arm of the binifer has from about 1 to about 25,000 isobutylene repeating units.

A polyisobutylene telechelic polymer made according to the present invention will thus have the following formula when m-t-BuDCC is utilized.

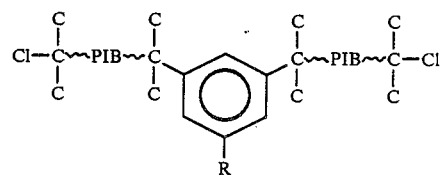

PIB represents the isobutylene repeating unit with the chlorine atom being located on each end thereof. The polymer produced utilizing m-t-BuDCB will be the same except for the possible existence of bromine on the end of each chain in lieu of the chlorine. When m-DMeDCC is utilized as the binifer, the following represents the structure of the polymer:

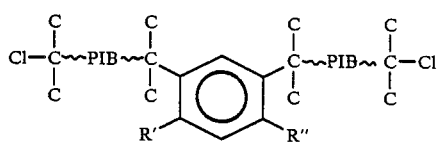

The formula will be the same for the brominated binifer except that bromine in lieu of the chlorine may exist on the chain end. The above two polymers containing chlorine groups on the end thereof are preferred.

The polymers produced according to the present invention are generally viscous liquids if the number of repeating units is up to approximately 10,000, and generally solid or rubbery if the number of repeating units is 10,000 or greater. They are generally chemically stable and can be utilized as colorless adhesives. Moreover, they can be converted to other compounds as set forth in U.S. Pat. Nos. 4,316,973; 4,342,849; 4,276,349; as well as 4,429,099, which are hereby fully incorporated by reference.

The invention will be better understood by reference to the following examples.

EXAMPLE 1

Preparation of m-t-BuDCC and m-t-BuDCB

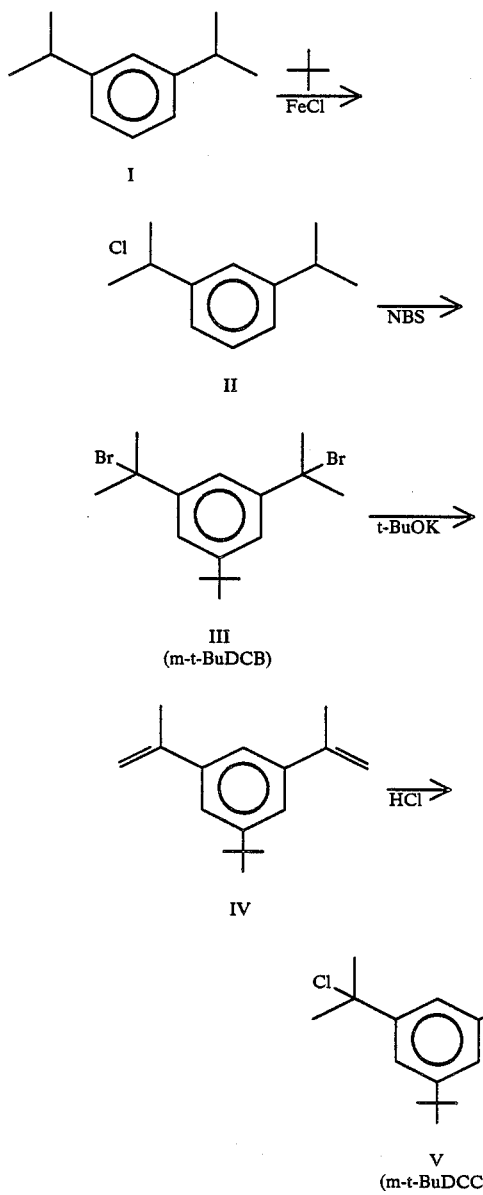

Tert-butyl chloride (20 ml, 0.18 moles) was added dropwise to a mixture of I (100 ml) and FeCl$_3$ (13 g, 0.08 moles) at 0° C. After the evolution of HCl, the mixture was washed with water, dried with CaCl$_2$, and distilled under vacuum. According to $^1$H NMR spectroscopy, the product was pure II; δ (ppm)=6.85 (aromatic, s, 3H), 2.8 (methine, m, 24), 1.25 (methyl, s, 12H) and 1.15 (methyl, s, 9H).

III, that is m-t-BuDCB, was prepared by adding II (22 g, 0.10 moles) to a stirred solution of N-bromosuccinimide (39 g, 0.22 moles) and benzoyl peroxide (5 g, 0.02 moles) in CCl$_4$ (200 ml). After reaching the boiling point of the solution, the NBS rises to the top (~1 min). The system was cooled with ice, filtered, and after evaporating the solvent (rotovap) the product was recyrstallized from n-hexane (Mp=75°-76° C.). $^1$H NMR spectroscopy showed essentially pure III; δ (ppm)=7.35 (aromatic, s, 3H), 2.15 (methyl, s, 12H), and 1.35 (methyl, s, 9H).

IV was prepared by dehydrobromination of III with t-BuOK. Thus, a solution of t-BuOK (25 g, 0.22 moles) in THF (250 ml) was added dropwise to a solution of III (18.8 g, 0.05 moles) in THF (250 ml) over a period of 30 min. at 0° C. Then the mixture was warmed slowly to room temperature. After 5 hours of stirring n-hexane (500 ml) was added. The product was washed with water, dried with CaCl$_2$ and vacuum distilled. According to $^1$H NMR spectroscopy, the colorless liquid appeared to be essentially pure IV, δ (ppm)=7.15 (aromatic, s, 3H), 5.14–4.95 (vinyl, d, 4H), 2.15 (methyl, s, 6H), and 1.35 (methyl, s, 9H).

The m-t-BuDCC was obtained by hydrochlorination of IV. Thus HCl was bubbled through a solution of IV (10 g, 0.905 moles) in CH$_2$Cl$_2$ (100 ml) at 0° C. for several hours. The solvent was removed and the product was recrystallized from n-hexane (Mp of colorless crystals=66.68° C.). H NMR δ (ppm)=7.6 (aromatic, s, 3H), 205 (methyl, s, 12H), 1,4 (methyl, s, 9H). C NMR: δ (ppm)=150.87 (aromatic, substituted), 145.69 (aromatic, substituted), 121.78 aromatic), 119.82 (aromatic), 69.98 (aliphatic, quarternary), 35.43 (aliphatic, quartenary), 34.38 (methyl), 31.35 (methyl).

The synthesis of the 1,3-di(3-chloro-1,1,3-trimethylbutyl)-5-tertbutylbenzene model compound was carried out by the same technique used for the preparation of 1,4-di(3-chloro-1,1,3-trimethylbutyl)benzene. The product obtained was a colorless liquid. $^1$H NMR: δ (ppm)=7.1 (aromatic, s, 3H), 2.35 (methylene s, 4H), 1.55 (methyl, s, 12H), 1.40 (methyl, s, 9H) and 1.35 (methyl, s, 12H).

EXAMPLE 2

Polymerization of isobutylene with m-t-BuDCC was carried out as follows:

1. Procedure

Into a 250 ml two-necked, round-bottom flask fitted with stirrer, are introduced under a ntirogen atmosphere 9 ml olefin-free n-hexane (Note 1), 65 ml (volume at minus 80° C.) methyl chloride (Note 2), and 3 ml (volume at minus 80° C.) boron trichloride (Note 3). The solution is stirred at minus 80° C. with the temperature and atmosphere being controlled with a liquid nitrogen cooled bath contained in a suitably equipped dry box (Note 4). Polymerization is initiated by the slow addition of a mixture of 1 g, 1,3-di(2-chloro-2-propyl)-5-tert-butyl-benzene, dissolved in 15 ml methyl chloride (volume at minus 80° C. (Notes 5,6,7) and 5.76 g (8 ml, volume at minus 80° C.) isobutylene (Note 8). The onset of reaction is marked by the appearance of a reddish-brown color and haziness. After each 50 minutes of stirring at minus 80° C., the polymerization is terminated by the introduction of 10 ml precooled methanol. The temperature is allowed to rise to ambient, the solvent is evaporated, and the product is stirred with 100 ml n-hexane for 30 minutes. The mixture is repeatedly washed with water and slightly acidic water (Note 9) followed by distilled water until a clear hexane layer is obtained. The hexane solution is dried overnight by anhydrous sodium sulfate. Finally, the product is filtered (Note 10), the n-hexane is evaporated (rotavap) at room temperature and the polymer is further dried under reduced pressure overnight. The crude polymer yield is ~100 percent, however, due to unavoidable losses during purification, the final yield is 6.08 g (90 percent).

2. Characterization

The polymer is a transparent liquid. $^1$H NMR spectroscopy shows resonances at 1.65, 1.85, and at 7.15 ppm which is in agreement with the structure IV shown above for $\alpha,\omega$-di(tert-chloro)polyisobutylene (Note 11). The number average molecular weight determined by gel permeation chromatography and vapor pressure osmometry is 1400±100 g/mole (Note 12 and 13).

3. Notes

1. Olefin-free n-hexane was prepared by refluxing n-hexane with fuming sulfuric acid (n-hexane:H$_2$SO$_4$=10:1 by volume) for about 15–20 hours followed by several washings with water and drying over anhydrous CaCl$_2$. The product was distilled over CaH$_2$ under nitrogen before use.

2. Gaseous methyl chloride (Research Grade, Matheson and Co.) was dried by passing it through tubes filled with porous barium oxide and powdery molecular sieves (Linde, 4 Å). The gas was condensed into a measuring cylinder dipped in the cooling bath at minus 80° C. and the liquid was transferred to the reactor.

3. Gaseous boron trichloride (Linde Co.) was condensed at minus 80° C. and the volume of the liquid was measured by a measuring cylinder.

4. A convenient dry box for carrying out low temperature polymerizations under an inert atmosphere has been described.

5. The mixture was added in a slow stream over a period of one minute.

6. One gram 1,3-di(2-chloro-2-propyl)-5-tert-benzene was dissolved in 15 ml methyl chloride at minus 80° C. by stirring and then the isobutylene was added.

7. This preparation has been described in Example 1.

8. Isobutylene (Matheson and Co.) was passed through tubes filled with powdery barium oxide and molecular sieves (Linde, 4 Å), condensed in a measuring cylinder at minus 80° C., and transferred to the reactor.

9. Acidic water was prepared by adding hydrochloric acid to water (1 percent v/v).

10. The sodium sulfate was rinsed three to four times with fresh n-hexane to minimize polymer losses.

11. $^1$H NMR spectroscopy was performed by the use of a Varian Associates T-60 NMR spectrometer at room temperature, with CCl$_4$ solvent and TMS standard.

12. GPC was performed by using a Waters Associates 6000 A high pressure instrument equipped with a Model 440 ultraviolet and a Model R401 differential refractometer detector, and five $\mu$-Styragel columns of pore sizes 10$^6$, 10$^5$, 10$^4$, 10$^3$ and 500 A. A calibration curve was constructed by using fractionated polyisobutylene samples of known molecular weights with narrow molecular weight dispersities ($\overline{M}_w/\overline{M}_n$=1.1–1.3). Approximately 0.4 ml of a 0.2 percent solution of Cl-PIB-Cl in tetrahydrofuran was used, with a flow rate of 1 ml/min.

13. VPO was performed using a Knauer Vapor pressure osmeter Model No. 11.00 (Utopia Instrument Company) and toluene solvent at 40° C.

In a manner similar to that above, the polymerization of isobutylene was carried out at various temperatures and the following data obtained.

TABLE I

Molecular Weights and Number Average Degrees of End Groups ($F_n$) of PIB's Obtained by the m-t-BuDCC/BCl$_3$ System)

| Temperature °C. | $\overline{M}_n$ g/mole | $\overline{M}_w$ g/mole | $\overline{M}_w/\overline{M}_n$ | $\overline{F}_n$ | Conversion Percent |
|---|---|---|---|---|---|
| −30 | 1700 | 3900 | 2.29 | 1.98 | 68.9 |
| −30 | 2100 | 4200 | 2.00 | — | — |
| −40 | 1800 | 3500 | 1.94 | 1.95 | 71.5 |
| −50 | 2300 | 5300 | 2.30 | 2.04 | 72.7 |
| −70 | 2200 | 4900 | 2.23 | 1.97 | 72.5 |
| −80 | 2200 | 4300 | 1.95 | 1.97 | 73.0 |

[IB] = 0.3 M, [m-t-BuDCC] = 6.72 × 10$^3$, [BCl$_3$] = 3.4 × 10$^{-2}$ M, CH$_3$Cl, 5 min.

As apparent from Table I, the molecular weight distribution ($\overline{M}_w/\overline{M}_n$) is rather narrow at all temperatures. Moreover, the number of end groups as represented by $F_n$ was approximately 2. Moreover, the percent conversion obtained was relatively high.

EXAMPLE 3

Polymerization of isobutylene by m-t-BuDCB/BCl$_3$ binifer system.

In a manner exactly identical to that set forth in Example 2, polymerization was carried out except that 1,3-di(2-bromo-2-propyl)-5-tert-butylbenzene was utilized, that is m-t-BuDCB as the binifer. When the reaction was carried out at minus 50° C., the data set forth in Table II was obtained.

TABLE II

Isobutylene Polymerization by the m-t-BuDCB and m-t-BuDCC/BCl$_3$ Systems at −50° C.

| Binifer | Solvent | Time min. | Conv. % | $\overline{M}_w$ g/mole | $\overline{M}_w$ g/mole | $\overline{M}_w/\overline{M}_n$ | $I_{eff}$ % | $\overline{F}_n$** |
|---|---|---|---|---|---|---|---|---|
| m-t-BuDCB | CH$_3$Cl | 5 | 81.4 | 5300 | 12100 | 2.27 | 72 | 2.0 ± 0.1 |
| m-t-BuDCB | CH$_3$Cl | 30 | 100 | 6300 | 13100 | 2.08 | 74 | 2.0 ± 0.1 |
| m-t-BuDCB | CH$_3$Cl/n-hexane | 5 | 69.5 | 6300 | 13400 | 2.14 | 53 | 2.0 ± 0.1 |
| m-t-BuDCB | CH$_3$Cl/n-hexane | 30 | 90.9 | 7300 | 16000 | 2.18 | 58 | 2.0 ± 0.1 |
| m-t-BuDCC | CH$_3$Cl | 5 | 71.4 | 1800 | 3700 | 2.1 | 99 | 2.0 ± 0.1 |
| m-t-BuDCC | CH$_3$Cl | 30 | 75.2 | 3700 | 7600 | 2.03 | 100 | 2.0 ± 0.1 |
| m-t-BuDCC | CH$_3$Cl/n-hexane | 5 | 70.9 | 3000 | 9300 | 3.14 | 100 | 2.0 ± 0.1 |
| m-t-BuDCC | CH$_3$Cl/n-hexane | 30 | 76.1 | 4200 | 11800 | 2.8 | 93 | 2.0 ± 0.1 |

TABLE II-continued

Isobutylene Polymerization by the m-t-BuDCB and m-t-BuDCC/BCl3 Systems at −50° C.

| Binifer | Solvent | Time min. | Conv. % | $\overline{M}_w$ g/mole | $\overline{M}_w$ g/mole | $\overline{M}_w/\overline{M}_n$ | $I_{eff}$ % | $\overline{F}_n$** |
|---|---|---|---|---|---|---|---|---|
| | n-hexane | | | | | | | |

[Binifer] = 4.9 × 10$^{-3}$ M, [IB] = 0.41 M, [BCl3] = 2.45 × 10$^{-2}$ M, CH3Cl/n-hexane 76/17 v/v, −50° C.
*[Binifer] = 6.72 × 10$^{-3}$ M, IB = 0.3 M
**Obtained by $^1$H NMR after dehydrohalogenation As apparent from Table II, the percent conversion generally increased with time. Moreover, in all examples, the number of end groups was very close to 2.0. Generally, as indicated by the last half of Table II, the efficiency of the chlorine-containing binifer was greater than that of the bromo-containing binifer. Otherwise, both binifers yielded narrow molecular weight ratios.

EXAMPLE 4

Synthesis of 1,3-di(2-chloro-2-propyl)-4,6-dimethylbenzene (m-DMeDCC): m-Xylene was diacetylated to produce 1,3-dimethyl-4,6-diacetophenone. The produce was purified by recrystallization from ether followed by sublimation (yield=5%) and characterized by H NMR spectroscopy (CCl4): δ (ppm): 7.85 (aromatic, s, H), 6.95 (aromatic, s, H), 2.55 (methyl, s, 6H) and 2.50 (methyl, s, 6H). The 1,3-dimethyl-4-6-diacetophenone was converted into 1,3-di(2-hydroxy-2-propyl)4,6-dimethylbenzene by a Grignard (CH3MgI/ether) reaction. It was recrystallized from ethylacetate and characterized by H NMR (DMSO-d6): δ (ppm): 7.45 (aromatic, s, H), 6.75 (aromatic s, H,), 4.65 (hydroxy, s, 2H), 2.40 (methyl, s, 6H), and 1.50 (methyl, s, 12H). Finally, this compound was hydrochlorinated (HCl gas in CH2Cl2, 5 hours, 0° C.) to give 1,3-di(2-chloro-2-propyl)-4-6-dimethylbenzene. The white crystalline product was recrystallized from n-hexane and characterized by H NMR spectroscopy (CCl4): δ (ppm): 7.30 (aromatic, s, H), 6.82 (aromatic, s, H), 2.55 (methyl, s, 6H) and 1.95 (methyl, s, 12H).

In a manner similar to that above, the bromine-containing binifer can be produced by following the same procedure except that in the last step, instead of being hydrochlorinated, it is hydrobrominated.

EXAMPLE 5

Polymerization of the m-DMeDCC binifer with isobutylene was carried out in the following manner.

In a manner exactly identical as set forth in Example 2, a polymerization was conducted except that the binifer was said m-DMeDCC.

Utilizing such a polymerization at minus 30° C., the data set forth in Table III was obtained.

TABLE III

Polymerization of Isobutylene by the m-t-BuDCC/BCl3 Binifer System at Various Monomer Concentrations at −30° C.*

| [M] M | Converation % | $\overline{M}_n$ g/mole | $\overline{M}_w$ g/mole | $\overline{M}_w/\overline{M}_n$ |
|---|---|---|---|---|
| 0.29 | 84.65 | 2700 | 7900 | 2.91 |
| 0.29 | 84.36 | 2800 | 9500 | 3.4 |
| 0.348 | 87.06 | 3100 | 13000 | 4.25 |
| 0.348 | 83.39 | 3600 | 11700 | 3.29 |
| 0.499 | 91.0 | 4600 | 17800 | 3.88 |
| 0.499 | 86.76 | 4500 | 15600 | 3.48 |
| 0.755 | 92.98 | 8400 | 24500 | 2.93 |
| 0.755 | 87.35 | 7300 | 25100 | 3.44 |
| 0.998 | 89.70 | 9400 | 24200 | 2.57 |
| 0.998 | 83.44 | 8300 | 29700 | 3.6 |

*[Inifer] - 6.72 × 10$^3$ M, [BCl3] = 3.36 × 10$^{-2}$ M, CH3Cl/hexane (15–21%), 5 min., −30° C.
Linear regression coefficient r = 0.988

As apparent from Table III, good conversion was obtained along with a farily low molecular weight ratio.

When the same polymerization reaction was carried out at minus 20° C., the following data were obtained.

TABLE IV

Polymerization of Isobutylene by the m-t-BuDCC/BCl3 Binifer System at Various Monomer Concentrations at −20° C.*

| [M] | Conversion % | $\overline{M}_n$ g/mole | $\overline{M}_w$ g/mole | $\overline{M}_w/\overline{M}_n$ |
|---|---|---|---|---|
| 0.29 | 8.7 | 2500 | 4500 | 1.9 |
| 0.34 | 8.9 | 2800 | 5300 | 1.9 |
| 0.50 | 10.7 | 4100 | 8400 | 2.0 |
| 0.99 | 11.7 | 7500 | 16600 | 2.57 |

*[Inifer] = 2.79 × 10$^{-3}$ M, [BCl3] = 1.4 × 10$^{-2}$ M, CH2Cl2, n-hexane (15–20%), 5 min., −20° C.
Linear regression coefficient r = 0.9997

As apparent from Table IV, the conversion was much lower and, accordingly, generally indicating the limit of the polymerization temperature.

In order to demonstrate the effect of temperature, polymerization was carried out as set forth in Table V.

TABLE V

Polymerization of Isobutylene by the m-t-BuDCC/BCl3 Binifer System Under Various Conditions*

| [m-t-BuDCC] M × 10$^3$ | Conversion % | Temperature °C. | Solvent | $\overline{M}_n$ g/mole | $\overline{M}_w$ g/mole | $\overline{M}_w/\overline{M}_n$ |
|---|---|---|---|---|---|---|
| 6.3 | 69.6 | −30 | CH3Cl/n-hexane | 2500 | 8500 | 3.35 |
| 4.93 | 64.2 | −30 | " | 2700 | 9700 | 3.6 |
| 3.50 | 58.3 | −30 | " | 3700 | 10700 | 2.9 |
| 2.47 | 54.3 | −30 | " | 5300 | 13900 | 2.6 |
| 1.4 | 36.4 | −30 | " | 6600 | 15600 | 2.38 |
| 5.6 | 68.9 | −50 | " | 3300 | 9600 | 2.87 |
| 4.96 | 70.9 | −50 | " | 3000 | 9300 | 3.14 |
| 4.2 | 66.65 | −50 | " | 4100 | 10700 | 2.61 |
| 3.5 | 66.5 | −50 | " | 4400 | 11100 | 2.53 |
| 2.4 | 59.1 | −50 | " | 5200 | 12500 | 2.4 |
| 2.54 | 60.6 | −50 | " | 5700 | 13400 | 2.36 |
| 1.52 | 45.4 | −50 | " | 7600 | 16500 | 2.16 |

TABLE V-continued
Polymerization of Isobutylene by the m-t-BuDCC/BCl₃ Binifer System Under Various Conditions*

| [m-t-BuDCC] M × 10³ | Conversion % | Temperature °C. | Solvent | $\bar{M}_n$ g/mole | $\bar{M}_w$ g/mole | $\bar{M}_w/\bar{M}_n$ |
|---|---|---|---|---|---|---|
| 5.62 | 76.5 | −80 | " | 3000 | 8500 | 2.87 |
| 4.97 | 73.2 | −80 | " | 3500 | 9200 | 2.7 |
| 4.88 | 74.6 | −80 | " | 3400 | 8700 | 2.54 |
| 4.26 | 72.9 | −80 | " | 3700 | 9800 | 2.65 |
| 3.52 | 65.8 | −80 | " | 4900 | 10600 | 2.17 |
| 2.48 | 63.8 | −80 | " | 6900 | 13800 | 1.99 |
| 1.44 | 41.5 | −80 | " | 8400 | 14600 | 1.75 |
| 6.36 | 76.6 | −50 | CH₃Cl | 4600 | 12600 | 2.73 |
| 4.9 | 77.5 | −50 | " | 6000 | 1500 | 2.51 |
| 3.53 | 71.1 | −50 | " | 8000 | 17600 | 2.2 |
| 2.48 | 71.3 | −50 | " | 11100 | 20400 | 1.83 |
| 1.44 | 67.3 | −50 | " | 17300 | 26100 | 1.5 |

*[IB] = 0.41 M, [BCl₃]/m-t-BuDCC = 5, CH₃Cl/n-hexane - 75/17, 5 min.

As apparent from this table, generally good conversion was obtained through a wide range of temperature ranges. Moreover, the molecular weight ratio was rather low except for several examples conducted at minus 30° C.

While in accordance with the patent statutes, a best mode and preferred embodiment has been described in detail, the invention is not limited thereto, rather the invention is measured by the scope of the attached claims.

What is claimed:

1. A telechelic polymer prepared from a sterically hindered binifer, comprising:
   the polymer, said polymer made by reacting isobutylene with the sterically hindered binifer, said sterically hindered binifer having the formula

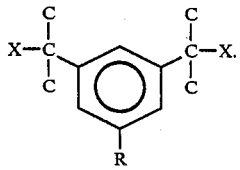

where R is an alkyl having from about 1 to about 5 carbon atoms or a cycloalkyl having from 4 to 8 carbon atoms, where X is Cl or Br.

2. A telechelic polymer according to claim 1, wherein X is chlorine, and R is tertiary butyl.

3. A telechelic polymer having the formula

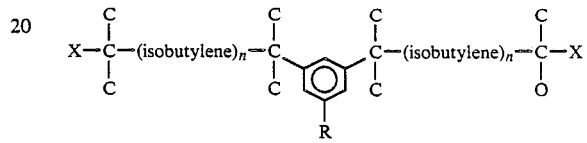

where R is an alkyl having from 1 to 5 carbon atoms or a cycloalkyl having from 4 to 8 carbon atoms, where X is chlorine or bromine, and wherein n is from 1 to 25,000.

4. A telechelic polymer according to claim 3, where n is 1 to 200.

5. A telechelic polymer according to claim 4, wherein R is tertiary butyl.

6. A telechelic polymer according to claim 5, wherein X is chlorine.

7. A telechelic polymer having the formula

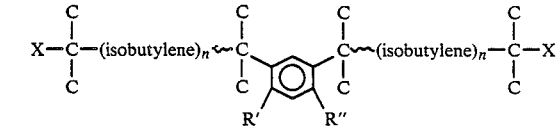

wherein R' and R" can be the same or different, wherein R' and R" is an alkyl group having from 1 to 5 carbon atoms or a cycloalkyl group having from 4 to 8 carbon atoms, wherein X is chlorine or bromine, and wherein n is from 1 to about 50,000.

8. A telechelic polymer according to claim 7, wherein n is from 1 to about 200.

9. A telechelic polymer according to claim 8, wherein R' and R" are methyl.

10. A telechelic polymer according to claim 9, wherein X is chlorine.

* * * * *